United States Patent [19]

Ferrer et al.

[11] Patent Number: 4,923,024

[45] Date of Patent: May 8, 1990

[54] APPARATUS FOR WEIGHTING AND MEASURING THE STATURE OF PERSONS

[76] Inventors: Jose M. S. Ferrer, C. Padua, 86-88, 08006 Barcelona; Jose N. Pajares, C. Cultura, 15, Santa Coloma De Gramenet Barcelona; Manuel T. Torres, C. Sant Bru, 210, 08911 Badalona (Barcelona), all of Spain

[21] Appl. No.: 375,745

[22] Filed: Jul. 5, 1989

[30] Foreign Application Priority Data

Jul. 18, 1988 [ES] Spain ................................ 8802582

[51] Int. Cl.⁵ .................... G01G 19/00; G01G 23/38
[52] U.S. Cl. ........................................ 177/245; 177/4
[58] Field of Search ................................ 177/245, 4

[56] References Cited

U.S. PATENT DOCUMENTS

| | | | |
|---|---|---|---|
| 3,616,690 | 11/1971 | Harden | 177/245 X |
| 4,336,855 | 6/1982 | Chen | 177/245 |
| 4,518,052 | 5/1985 | Chen | 177/245 |

FOREIGN PATENT DOCUMENTS 55-12485  1/1980  Japan ................................ 177/245

Primary Examiner—George H. Miller, Jr.
Attorney, Agent, or Firm—Steinberg & Raskin

[57] ABSTRACT

Comprises a device (1) for measuring the stature of persons and an electronic scales (2) controlled by one and the same microprocessor (13).

The device (1) for measuring the stature of persons comprises an emitter/receiver device (3), a height display device (4), a luminous device (5) for indicating the end of the stature measuring operation, an acoustic indicator device (6), a plurality of switches: coin detector switch (7), coin selector switch (8), and fast-reading/slow-reading commuter (9). The amplifier of the emitter/receiver device is of variable gain to linearize the signal.

The electronic scales comprises a load cell (10), an analogic/digital converter device (11), a weight display device (12) and a device (19) for storage of the zero and bottom of scale values.

Comprises a printer (20), with its controller, providing the ideal weight corresponding to each stature.

5 Claims, 4 Drawing Sheets

APPARATUS FOR WEIGHTING AND MEASURING THE STATURE OF PERSONS

The present invention relates to an apparatus for weighting and measuring the stature of persons.

BACKGROUND OF THE INVENTION

There are well known devices for measuring the stature of persons. Such devices generally include an emitter/receiver device which emits an electric signal in the form of an ultrasonic pulse, and, conversely, transforms a received ultrasonic pulse to an electric signal, a microprocessor, a device for displaying the stature of the examined person, and at least one device indicating the end of the stature measuring operation. The microprocessor communicates with the emitter/receiver device, with the display device and with at least an indicating device, through an input/output port and the corresponding buffers. The emitter/receiver device includes a transducer transforming an electric signal to an ultrasonic pulse in both emission and receive directions, an oscillator connected to the transducer in the emitting network, and a filter, an amplifier and an alternating/continuous converter series connected in the receive network.

Such apparatus for measuring the stature of persons suffer from the drawback that the amplifier gain is constant, so that its behavior at different distances is not optimum. If the gain is made high in order that the amplification is enough for great distances, it becomes too high for small distances and picks up noises providing wrong signals.

There are known as well electronic scales comprising a load cell, an analogic/digital converter device, a microprocessor and a display for the weight placed onto the load cell. The microprocessor communicates with the analogic/digital converter device and the display through an input/output port.

These scales show the drawback that it is necessary to adjust the zero or offset and the bottom of scale or gain, for each scales.

On the other hand, owing to the functional relation binding the person weight and stature, there is a experienced need for an integrated apparatus for measuring the stature of persons and electronic scales adapted to furnish, besides of their own data about the stature and the weight of a person in one and the same apparatus, as well a comparison of the indicated weight with the ideal weight corresponding to the indicated stature of the same person.

DESCRIPTION OF THE INVENTION

The apparatus for weighing and measuring the stature of persons which makes the subject of the invention is featured by the fact that the device for measuring the stature and the scales are connected to one and the same microprocessor, and the apparatus has a weight display and a stature display; by the fact that it comprises a printer providing, for each stature, the corresponding ideal weight according to the data stored in the microprocessor; and by the fact that the amplifier of the emitter/receiver device is of a variable gain in function of time with a view of linearizing the signal received in the emitter/receiver device as a function of the distance.

This linearization of the signal allows to surpass the above drawback of the known devices for measuring the stature of persons since for small distances a low gain is obtained which does not risk to pick up undesirable noises and, at the same time, for great distances, a gain high enough to suitably pick up the signal is obtained.

The apparatus limits as well the saturation of the receiver for echoes of bodies located at very short distance.

The linearization is obtained by making the gain to increase according to a parabolic pattern as a function of time.

To advantage, the amplifier of variable gain in function of the time comprises an operational amplifier and a variable gain control unit.

The said variable gain unit may be developed according to several manners: in analogic version or in digital version.

According to a digital embodiment, the apparatus of the invention comprises a plurality of resistors connected to a multiplexer in turn connected to a counter receiving clock pulses. In this embodiment, a polygonal approach to the parabolic curve of the gain is obtained.

Also to advantage, the electronic scales comprises a device for storing the zero and bottom of scale values and thus the scales must be adjusted only one time, the weight being obtained at each weighting operation by an interpolation between the stored zero and bottom of scale values.

The device for storing the zero and bottom of scale values comprises a programmable memory and a memory decoder connected to the microprocessor.

When no weight is on the scales platform, the microprocessor program continuously reads the weight value generated by the load cell and assumes that this value is the zero value. When a weight is placed onto the platform, the load cell detects a sudden variation and the last stable zero reading is congealed.

The bottom of scale value is adjusted one single time by means of a known weight, and it becomes stored in memory.

The obtention of a particular weight is calculated by interpolating between the already obtained zero and bottom of scale values.

BRIEF DESCRIPTION OF THE DRAWINGS

For a better understanding of the above exposition, some drawings are enclosed wherein a practical diagrammatic case of embodiment is represented only by way of a non restrictive example. In the said drawings.

DESCRIPTION OF PREFERRED EMBODIMENTS

Figure 1:
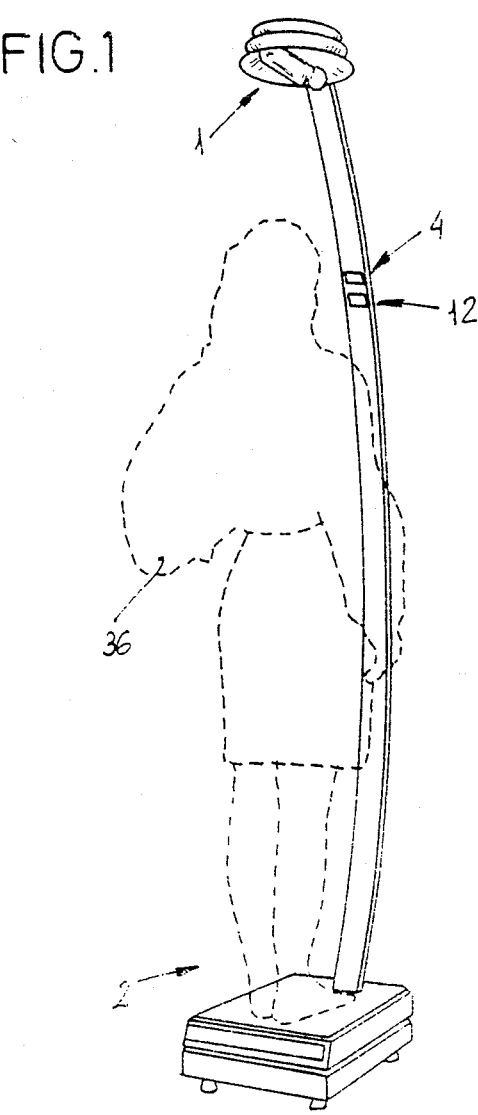
FIG. 1 is an isometric view of the apparatus according to the invention.
Figure 2:
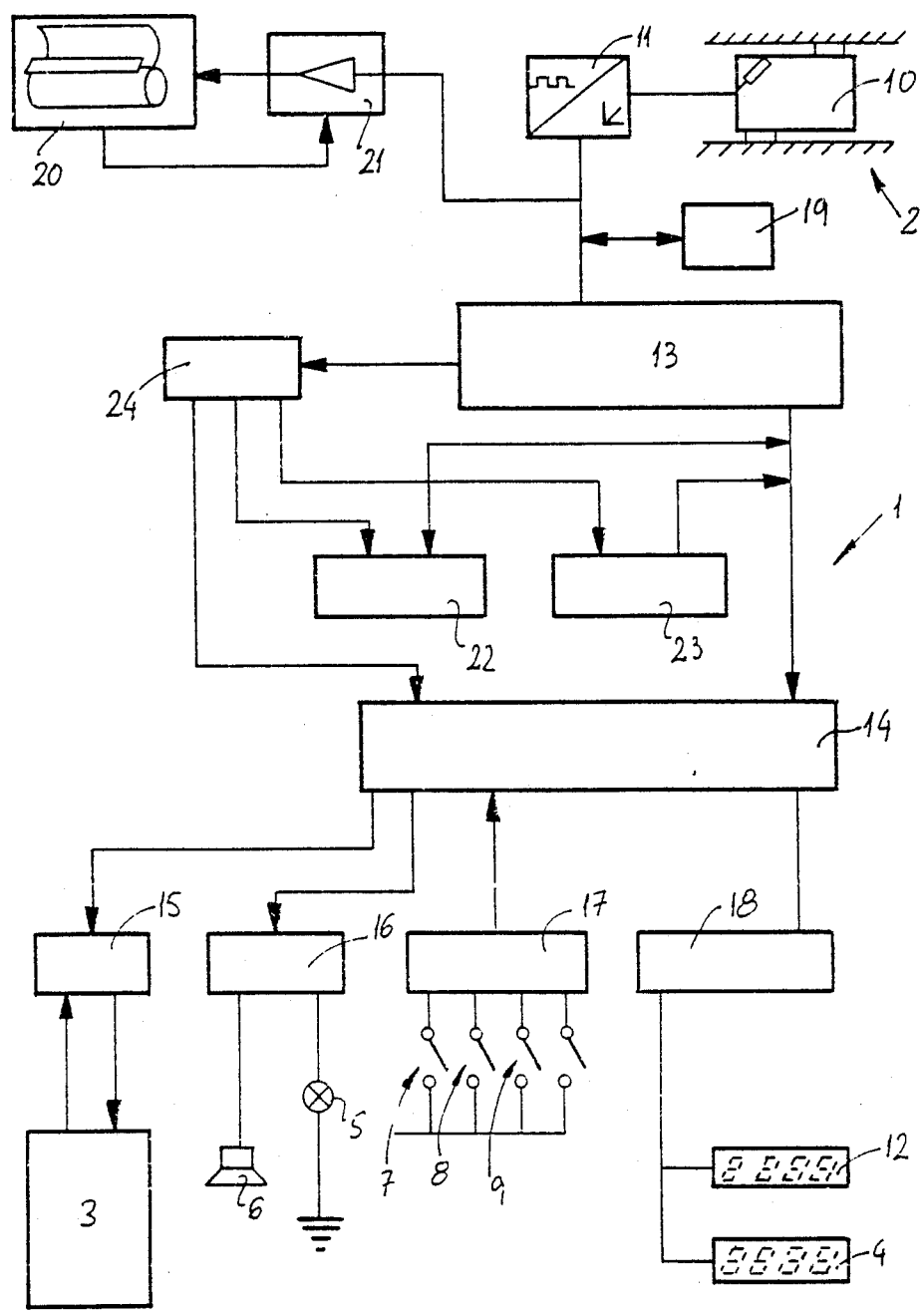
FIG. 2 is a functional block diagram of the same apparatus.

As shown in FIGS. 1 and 2, the apparatus for weighing and measuring the stature of persons, according to the invention, comprises a device 1 for measuring the stature of persons and a electronic scales 2.

The device for measuring the stature of persons comprises an emitter/receiver device 3 transforming an electric signal to an ultrasonic pulse which is emitted, and, conversely, transforms a received ultrasonic pulse to an electric signal, a device 4 for displaying the stature of the examined person, a luminous indicating device 5 for the end of the stature measuring operation, an acoustic indicator device 6 and a plurality of switches: coin detector 7, coin selector 8, and fast-reading/slow-reading commutator 9.

The electronic scales comprises a load cell 10, an analogic/digital converter device 11 and a display 12 for the weight placed onto the load cell.

The common microprocessor 13 controlling the device 1 for measuring the stature of persons and the electronic scales 2 is connected with the emitter/receiver device 3, with the indicator devices 5 and 6, with the switches 7,8,9 and with the displays 4 and 12 through an input/output port 14 and the corresponding buffers 15, 16,17,18.

The apparatus comprises as well a device for storing the zero and bottom of scale values 19 of the scales, a printer 20 and a controller 21.

The RAM memories and EPROM memories 23 as well as the decoder 24, are located next to the microprocessor 13.

The amplifier of the emitter/receiver device 3 is a time variable gain amplifier in order to linearize the signal received from the emitter/receiver device as a function of the distance.

Figure 3:
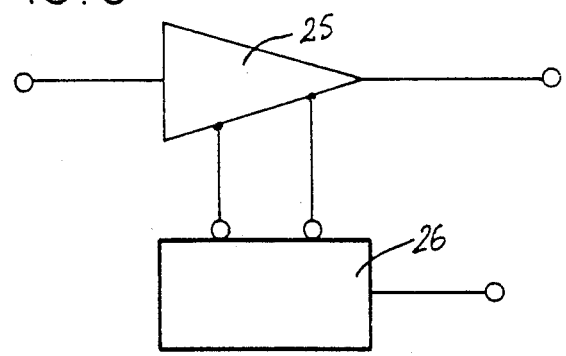
FIG. 3 is a diagram of the variable gain amplifier of the emitter receiver device.

FIG. 3 shows a diagram of the said amplifier, comprising an operational amplifier 25 and a variable gain control unit 26.

Figure 4:
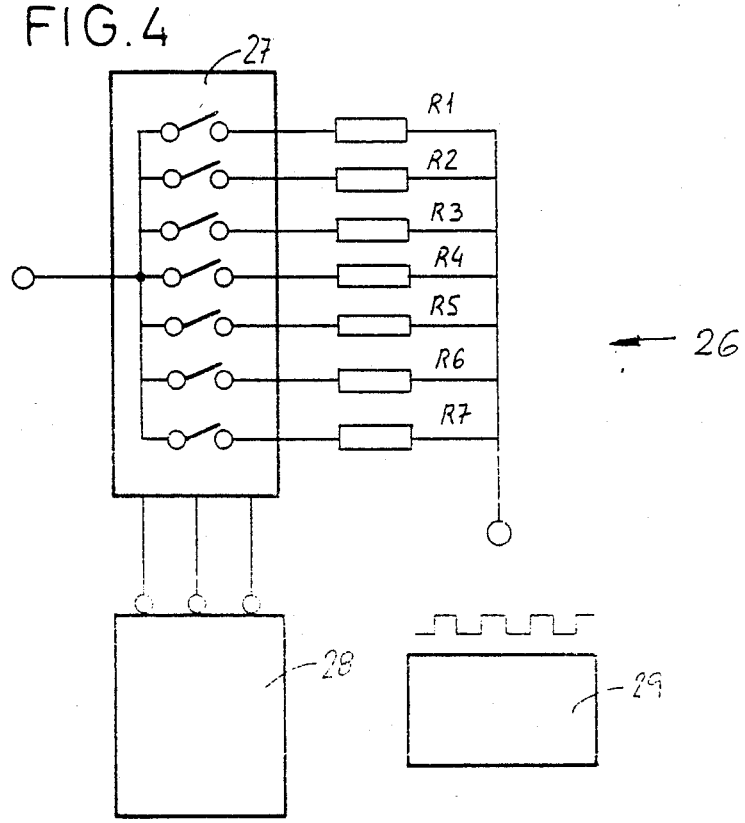
FIG. 4 is a diagram of a variable gain control unit.

According to a digital embodiment, shown in FIG. 4, the variable gain control unit 26 comprises a plurality of resistors R1 to R7 connected to a multiplexer 27 in turn connected to a counter 28 receiving clock pulses 29.

Figure 6:
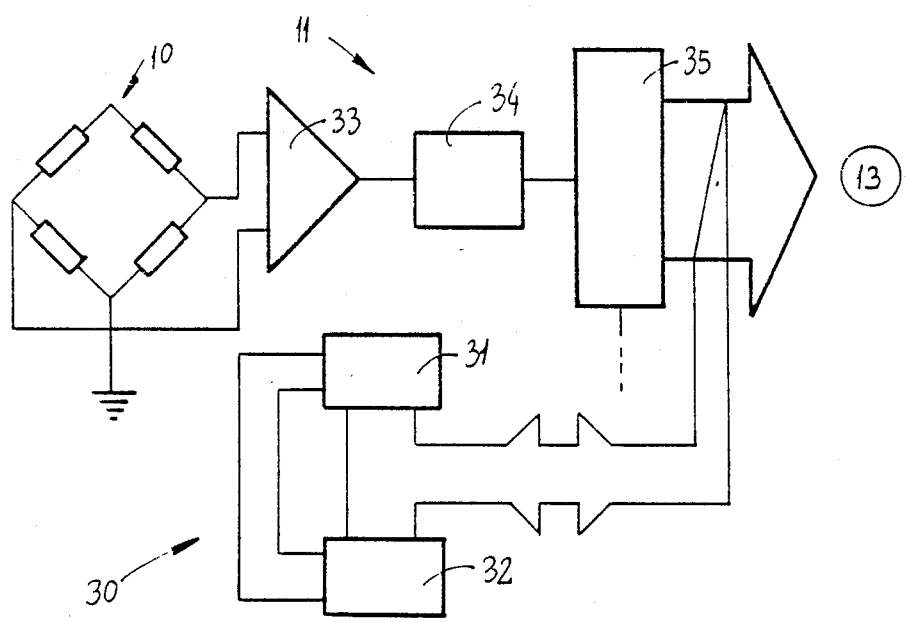
FIG. 6 is a functional block diagram of the scales endowed with a device for storing the zero and bottom of scale values.

FIG. 6 shows the electronic scales comprising a device 30 for storing the zero and bottom of scale values, which in turn comprises a programmable memory 31 and a memory decoder 32 connected to the microprocessor 13.

The Figure also shows the load cell 10 and the analogic/digital converter 11, which in turn comprises a analogic section formed of a differential amplifier 33 and a filter 34, and a digital section 35.

The operation of the apparatus according to the invention is as follows:

When a person 36 gets on the platform 2, the emitter/receiver sends and receives a signal which, suitably handled, shows on the display 4 the stature of the said person.

The amplifier of the emitter/receiver behaves such that the signal is linearized in function of time, that is to say, in function of the distance. To this end, it is necessary that the gain G increases according to a parabolic trend as a function of time t, such as shown by the curve of FIG. 5.

Figure 5:
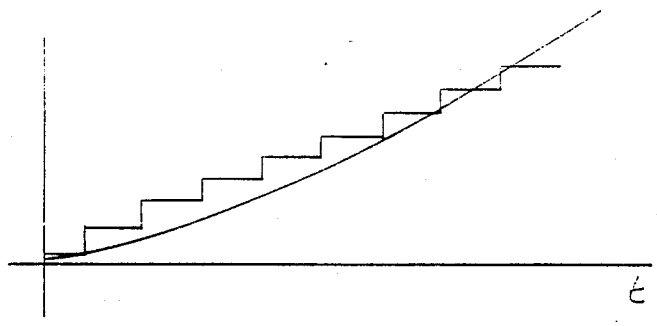
FIG. 5 shows the amplifier gain curve in function of time.

In the digital embodiment shown in FIG. 4, a polygonal approach to the parabolic curve of the gain is obtained, as it may be seen in FIG. 5.

As indicated above, it is necessary to adjust the scales 2 only one time, and the weight of each weighting operation is obtained by interpolating between the stored zero and bottom of scale values.

The above description corresponds to a specific embodiment of the invention, and all of the possible variations which are accessible to an expert are to be understood as comprised within the scope of the same.

We claim:

1. Apparatus for weighing and measuring the stature of persons, of the type comprising a device for measuring the stature of a person (1) and an electronic scales (2), the device for measuring the stature being of the type including an emitter-receiver device (3) transforming an electric signal to an ultrasonic pulse which is emitted, and transforming a received ultrasonic pulse to an electric signal, a microprocessor, a device (4) for displaying the stature of the examined person, and at least one device (5) indicating the end of the stature measuring operation, the microprocessor being communicated with the emitter/receiver device (3), with the display device (4) and with at least an indicator device (5,6), through an input/output port (14) and buffers (15,16,17,18), the emitter-receiver device (3) including a transducer (11) transforming an electric signal to an ultrasonic pulse in both emission and receive directions, an oscillator connected to the transducer in the emitting network, and a filter, an amplifier and an alternating/continuous converter series connected in the receive network, and the electronic scales being of the type including a load cell, an analogic/digital converter device, a microprocessor and a display for the weight placed onto the load cell, the microprocessor being in communication with the analogic/digital converter device and the display through an input/output port, characterized in that the device (1) for measuring the stature of persons and the scales (2) are connected to one and the same microprocessor (13), and the apparatus has a weight display and a stature display (4), the apparatus also comprises a printer (20) providing, for each stature, the corresponding ideal weight according to the data stored in the microprocessor (13), and the amplifier of the emitter/receiver device is of a variable gain in function of time with a view of linearizing the signal received in the emitter/receiver device as a function of the distance.

2. Apparatus according to claim 1, characterized by the fact that the variable gain amplifier in function of the time comprises an operational amplifier (25) and a variable gain control unit (26).

3. Apparatus according to claim 2, characterized by the fact that the variable gain control unit (26) comprises a plurality of resistors (R1-R7) connected to a multiplexer (27) in turn connected to a counter (28) receiving clock pulses (29).

4. Apparatus according to claim 1, characterized by the fact that the electronic scales (2) comprises a device (19) for storing the zero and bottom of scale values and thus the scales must be adjusted only one time, the weight being obtained at each weighing operation by an interpolation between the stored zero and bottom of scale values.

5. Apparatus according to claim 4, characterized by the fact that the device (19) for storing the zero and bottom of scale values comprises a programmable memory (23) and a memory decoder (24) connected to the microprocessor (13).

* * * * *